United States Patent [19]
Chodorge et al.

[11] Patent Number: 5,877,365
[45] Date of Patent: Mar. 2, 1999

[54] PROCESS AND PLANT FOR THE CONVERSION OF OLEFINIC $C_4$ CUTS TO POLYISOBUTENE AND TO PROPYLENE

[75] Inventors: Jean-Alain Chodorge, Antony; Dominique Commereuc, Meudon; Jean Cosyns, Maule; Didier Duee, Eragny sur Oise; Bernard Torck, Boulogne sur Seine, all of France

[73] Assignee: Institut Francais du Petrole, France

[21] Appl. No.: 644,159

[22] Filed: May 10, 1996

[30] Foreign Application Priority Data

May 11, 1995 [FR] France .................................. 95/05.560

[51] Int. Cl.⁶ .................................. C07C 2/02; C07C 6/02
[52] U.S. Cl. ........................... 585/329; 585/324; 585/326; 585/327; 585/329; 585/518; 585/643; 585/644; 585/646; 585/642
[58] Field of Search ..................... 585/324, 326, 585/327, 329, 518, 520, 525, 524, 532, 643, 644, 646, 647

[56] References Cited

U.S. PATENT DOCUMENTS

| | | | |
|---|---|---|---|
| 3,501,551 | 3/1970 | Heidler et al. | 260/683.15 |
| 3,728,414 | 4/1973 | Helden et al. | 585/646 |
| 4,132,745 | 1/1979 | Amigues et al. | 260/683.2 |
| 4,287,378 | 9/1981 | Pennella et al. | 585/643 |
| 4,324,938 | 4/1982 | Cosyns et al. | 585/332 |
| 4,558,170 | 12/1985 | Chen et al. | 585/532 |
| 5,414,179 | 5/1995 | Hunt et al. | 585/519 |
| 5,449,852 | 9/1995 | Chauvin et al. | 585/647 |

FOREIGN PATENT DOCUMENTS

| | | |
|---|---|---|
| 0 213 401 | 3/1987 | European Pat. Off. . |
| 2 442 246 | 6/1980 | France . |
| 2 709 125 | 2/1995 | France . |
| 72013251 | 12/1967 | Japan . |

OTHER PUBLICATIONS

Abstract, Database WPI, Section Ch, Wk. 7217, (JP–B–47 013 251), Derwent Publications Ltd., London, GB.

*Primary Examiner*—Glenn Caldarola
*Assistant Examiner*—Thuan D. Dang
*Attorney, Agent, or Firm*—Millen, White, Zelano, & Branigan, P.C.

[57] ABSTRACT

The present invention concerns a process for the conversion of an olefinic $C_4$ cut to polyisobutene and to propylene by metathesis. The process comprises three successive steps: (1) selective hydrogenation of diolefins with simultaneous isomerisation of 1-butene to 2-butenes, (2) polymerisation of the isobutene, including optional prior extraction of the isobutene, (3) metathesis of 2-butene with ethylene. Part or all of the $C_4$ cut may originate from the metathesis of an olefinic $C_5$ cut with ethylene after hydroisomerisation of the $C_5$ cut. Application to $C_4$ and $C_5$ steam cracking cuts.

10 Claims, 1 Drawing Sheet

PROCESS AND PLANT FOR THE CONVERSION OF OLEFINIC $C_4$ CUTS TO POLYISOBUTENE AND TO PROPYLENE

BACKGROUND OF THE INVENTION

The present invention relates to a process for the conversion of an olefinic $C_4$ cut to polyisobutene and to propylene. Part or all of the $C_4$ cut may originate from the conversion of an olefinic $C_5$ cut. When the cuts originate from a steam cracking operation, a further aim of the present invention is to optimise the relative ethylene-propylene selectivity of the steam cracking procedure using this process.

Steam cracking of feeds constituted by light paraffin cuts supplies ethylene and propylene for the petrochemical industry. It also provides a number of other heavier products, in particular a $C_4$ hydrocarbon cut which contains mainly 1,3-butadiene, isobutene, n-butenes and butanes, accompanied by traces of acetylenic hydrocarbons, and a $C_5$ hydrocarbon cut which contains mainly $C_5$ diolefins, methylbutenes, n-pentenes and pentanes, accompanied by traces of acetylenic hydrocarbons.

Likewise, catalytic cracking of heavy hydrocarbon feeds, in particular fluid catalytic cracking (FCC), produces lighter products, among them a $C_4$ hydrocarbon cut which contains mainly isobutane, isobutene, n-butenes and butanes, accompanied by small quantities of 1,3-butadiene and acetylenic hydrocarbons, and a $C_5$ hydrocarbon cut which contains mainly pentanes, methylbutenes and n-pentenes, accompanied by small quantities of $C_5$ diolefins and acetylenic hydrocarbons.

Until recently, only the 1,3-butadiene and the isobutene were of use in the polymer industry, in particular in the tire industry for the former. An increase in tire lifetime and a relative stagnation of demand has led to a surplus of butadiene which is not used to any great extent. In contrast, isobutene has gained in importance as it can be used to synthesize polymers with many uses.

SUMMARY OF THE INVENTION

The present invention provides a process for the treatment of a $C_4$ hydrocarbon cut containing mainly isobutene, n-butenes, butanes and varying amounts of 1,3-butadiene, which includes the transformation of isobutene to polyisobutene, and which can transform 1,3-butadiene and n-butenes to propylene for polymerisation, for example. Part or all of the $C_4$ hydrocarbons may also originate from an olefinic $C_5$ cut which is mainly transformed, after hydroisomerisation, to propylene and a mixture of mainly 1-butene and isobutene by metathesis with ethylene.

The relative proportions of ethylene and propylene produced in a steam cracking operation can be modulated to a certain extent by changing the nature of the feed and modifying the cracking conditions (severity). However, an operating mode intended to produce a higher proportion of propylene inevitably produces larger quantities of $C_4$ cut, $C_5$ cut and heavier petrol fractions of poor quality.

A further aim of the present invention is to optimise the relative ethylene-propylene selectivity of the steam cracking procedure by treating the $C_4$ or $C_5$ steam cracking hydrocarbon cuts to produce, inter alia, propylene, thus enabling the relative proportions of ethylene and propylene to be adjusted without requiring a to change in the cracking severity.

More precisely, the object of the invention is to provide a process for the conversion of an olefinic $C_4$ cut to polyisobutene and to propylene, the cut containing mainly diolefins, 1-butene, isobutene and acetylenic impurities, said process comprising the following steps which are carried out successively:

1) selective hydrogenation of the diolefins and acetylenic impurities with simultaneous isomerisation of the 1-butene to 2-butenes, by passing said cut in the liquid phase over a catalyst comprising at least one metal selected from the group formed by nickel, palladium and platinum, deposited on a support, at a temperature of 20°–200° C., a pressure of 1–5 MPa, and a space velocity of 0.5–10 $h^{-1}$, with a $H_2$/diolefin (molar) ratio of 0.5 to 5, preferably 1 to 3, to obtain an effluent containing mainly 2-butene and isobutene, and containing practically no diolefins or acetylenic compounds;

2) polymerisation of the isobutene contained in the effluent from step 1 to polyisobutene, in the presence of an acid catalyst, at a temperature of –100° C. to +100° C., and at a pressure such that the reaction is carried out in the liquid phase, wherein the isobutene may be separated from the other constituents of the cut from step 1 before polymerisation, to obtain polyisobutene and a residual $C_4$ cut without a polymer;

3) metathesis of the residual $C_4$ cut with ethylene, in the presence of a catalyst comprising at least one rhenium oxide deposited on a support, at a temperature in the range 0° C. to 100° C., and at a pressure which is at least equal to the vapour pressure of the reaction mixture at the reaction temperature, to obtain an effluent containing propylene, metathesis being followed by separation of the propylene.

In the $C_4$ cut which is treated using the above process, the isobutene and the 1-butene may completely or partially originate from an olefinic C5 cut which can contain mainly diolefins, n-pentenes, methylbutenes and acetylenic impurities, which is subjected to a treatment comprising at least the two following steps which are carried out successively:

1) selective hydrogenation of the diolefins and acetylenic impurities with simultaneous isomerisation of the alpha olefins containing 5 carbon atoms to 2-pentenes and 2-methyl-2-butene, by passing said cut in the liquid phase over a catalyst comprising at least one metal selected from the group formed by nickel, palladium and platinum, and deposited on a support, at a temperature of 20°–200° C., a pressure of 1–5 MPa, and a space velocity of 0.5–10 $h^{-1}$, with a $H_2$/diolefin (molar) ratio of 0.5 to 5, preferably 1 to 3, to obtain an effluent containing mainly 2-pentene and 2-methyl-2-butene, and containing practically no diolefins or acetylenic compounds;

2) metathesis of at least a portion of the effluent from the preceding step with ethylene, in the presence of a catalyst comprising at least one rhenium oxide deposited on a support, at a temperature in the range 0° C. to 100° C., and at a pressure which is at least equal to the vapour tension of the reaction mixture at the reaction temperature, to obtain an effluent containing mainly propylene, 1-butene and isobutene, metathesis being followed by separation of the propylene;

3) introduction of the 1-butene and isobutene mixture to the selective hydrogenation step for the $C_4$ cut.

BRIEF DESCRIPTION OF THE DRAWINGS

FIG. 1 is an embodiment wherein polymerization of the isobutene occurs directly after a stage of selective hydroisomerization of a $C_4$ cut.

FIG. 2 utilizes a separation stage to remove isobutene before polymerization.

FIG. 3 add an upstream hydroisomerization stage of a $C_5$ cut followed by a metathesis stage with ethylene to produce propylene and a $C_4$ byproduct stream, the latter being treated in accordance with FIG. 1.

FIG. 4 is similar to FIG. 3, but employs a common metathesis stage for the $C_5$ hydroisomerizate and the effluent from the isobutene polymerization stage.

DETAILED DESCRIPTION OF DRAWINGS

Figure 2:
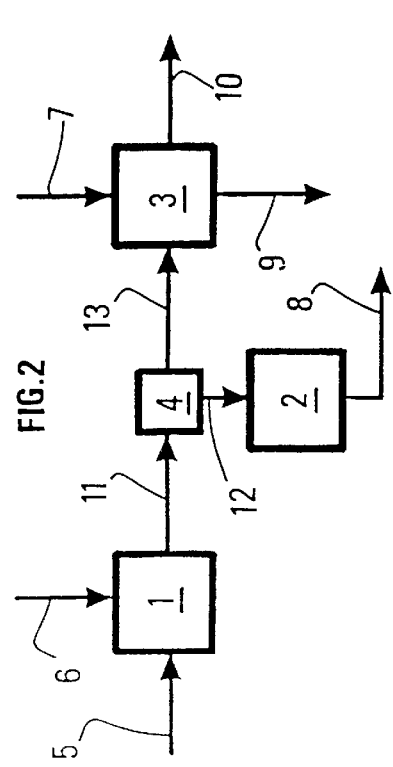
FIGS. 1–4 are black flow diagrams of various embodiments of the invention, as follows.

The process of the invention (illustrated in FIG. 1) will be described in more detail using a $C_4$ hydrocarbon cut containing mainly isobutene, n-butenes, butanes, and varying amounts of 1,3-butadiene, supplied via a line 5. The $C_4$ cut undergoes a succession of treatments which are consolidated in the following steps, to produce polyisobutene and propylene:

selective hydroisomerisation of 1,3-butadiene with isomerisation of 1-butene to 2-butene and hydrogenation of acetylenic hydrocarbons;

poly-nerisation of isobutene, optionally after separation of the isobutene from the other constituents of the cut from the first step, metathesis of the 2-butene—rich effluent in the presence of ethylene (ethenolysis) to produce propylene.

The succession of treatments of the process of the invention has a number of advantages. The most reactive compounds in the cut, namely the diolefins (for example 1,3-butadiene) which are in varying amounts, and the traces of acetylenic hydrocarbons, are transformed in the first step and thus do not cause side reactions in the following steps. Further, the selective hydroisomerisation of diolefins (for example 1,3-butadiene) in the steam cracking cuts can considerably increase the concentration of 2-butene in the cut, further enhancing the metathesis step and producing a high yield of propylene.

The principal aim of the first step is to transform 1,3-butadiene and n-butenes into 2-butene. 2-butene is the source of the propylene which is produced in the last metathesis step in the presence of ethylene. 1-butene does not produce a new product with the ethylene, and reacts with the 2-butene to produce propylene, but also to produce undesirable pentenes. Maximising the yield of 2-butene is thus desirable, i.e., to get as close as possible to the proportions dictated by thermodynamics. The second aim of this step is to eliminate the traces of acetylenic hydrocarbons which are always present in these cuts and which poison or pollute the subsequent steps.

In the first step (zone 1), the following reactions are carried out simultaneously, in the presence of hydrogen supplied via line 6:

selective hydroisomerisation of 1,3-butadiene to a mixture of n-butenes in thermodynamic equilibrium;

isomerisation of 1-butene to 2-butene, also in thermodynamic equilibrium;

hydrogenation of traces of acetylenic hydrocarbons.

These reactions can be carried out using various specific catalysts comprising one or more metals, for example from group 10 of the periodic classification (Ni, Pd, Pt), deposited on a support. Preferably, a catalyst is used which comprises at least one palladium compound fixed on a refractory mineral support, for example alumina. The amount of palladium on the support can be in the range 0.01% to 5% by weight, preferably in the range 0.05% to 1% by weight. A variety of known pretreatments may be applied to these catalysts to improve selectivity for the hydrogenation of 1,3-butadiene to butenes at the expense of complete hydrogenation to butane which must be avoided. The catalyst preferably contains 0.05% to 10% by weight of sulphur. Advantageously, the catalyst is constituted by palladium deposited on alumina and containing sulphur.

The catalyst can be sulphurized in situ (in the reaction zone) or preferably ex situ. In the latter case, the process described in French patent FR-93/09524 is preferably used, where the catalyst is treated, before being charged into the hydrogenation reactor, with at least one sulphur-containing compound diluted in a solvent, and the catalyst obtained containing 0.05% to 10% of sulphur (by weight) is charged into the reactor and activated in a neutral or reducing atmosphere at a temperature in the range 20° C. to 300° C., at a pressure in the range 0.1 to 5 MPa and at a GHSV in the range 50 to 600 $h^{-1}$, where the feed is brought into contact with the activated catalyst.

The mode of use of the catalyst which is preferably of palladium, is not critical, but it is generally preferred to use at least one downflow reactor with a fixed bed of catalyst. When the proportion of 1,3-butadiene in the cut is high, as is the case, for example, for a steam cracking cut when the 1,3-butadiene is not to be extracted for specific purposes, it may be of advantage to effect the transformation in two reactors in series to better control the hydrogenation selectivity. The second reactor may be an upflow reactor and may act as a finisher.

The quantity of hydrogen required for the reactions carried out in this step is adjusted as a function of the composition of the cut so that, advantageously, there is only a slight excess of hydrogen with respect to the theoretical stoichiometry.

The operating conditions are selected so that the reactants and products are liquid. It may, however, be of advantage to select an operating mode such that the products are partially vaporised at the reactor outlet, to facilitate thermal control of the reaction. The temperature can be between 20° C. and 200° C., preferably between 50° C. and 150° C., or more preferably between 60° C. and 150° C. The pressure can be adjusted to between 0.1 and 5 MPa, preferably between 0.5 and 4 MPa, advantageously between 0.5 and 3 MPa, so that the reactants are at least partially in the liquid phase. The space velocity can be in the range 0.5 to 10 $h^{-1}$, preferably in the range 1 to 6 $h^{-1}$, with a $H_2S$/diolefin (molar) ratio of 0.5 to 5, preferably 1 to 3.

Advantageously, the hydroisomerisation reactor or reactors is/are followed by a stabilizing column which eliminates traces of excess hydrogen and any methane.

The aim of the second step (zone 2) is to polymerise the isobutene present in the $C_4$ cut from the preceding step, for example to polyisobutene which can form part of the composition of elastomers, or to liquid polybutenes which can be used as additives for lubricants.

Figure 1:
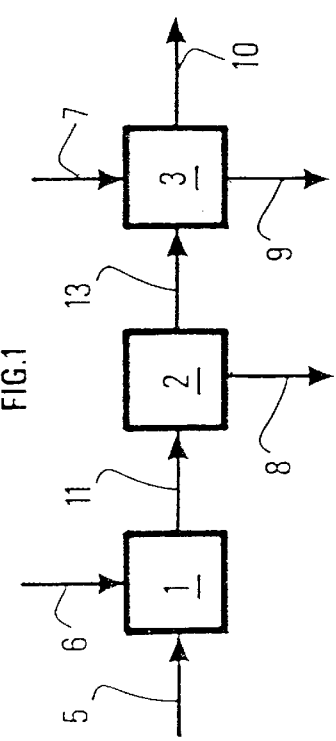

The effluent from step 1 (zone 1) supplied via line 11 can be treated as it stands (shown in FIG. 1).

In order to improve the quality of the products, it may be of interest to extract the isobutene from the effluent from the preceding step before polymerisation. This extraction can be carried out using any known method, for example by simple distillation, or by hydration of the isobutene to tertiary-butyl alcohol (in the presence of sulphuric acid, for example), followed by separation and dehydration of the alcohol to recover the isobutene, or by reaction with methanol in the presence of an acid ion exchange resin to transform the isobutene into methyl-tertiobutylether (MTBE) which can readily be separated by distillation then decomposed in the presence of an acid catalyst to liberate purified isobutene.

FIG. 2 shows this possibility with an isobutene separation zone 4.

Polymerisation is carried out using a Lewis acid catalyst, for example aluminium chloride, a chloroalkylaluminium, tin tetrachloride, or boron trifluoride, which may be combined with traces of a Bronsted acid such as hydrochloric acid, water, tertiary-butyl chloride, or organic acids. The catalyst can be used solid as a powder or in the form of a suspension in a saturated hydrocarbon such as hexane or isobutane, or in a halogenated hydrocarbon such as methyl chloride.

The operating conditions are chosen so that the reaction temperature can be precisely controlled. In general, the temperature is fixed so that the reaction occurs at a sufficient rate, for example from −100° C. to +100° C., preferably −50° C. to +50° C., and the pressure is adjusted so that, for example, the hydrocarbon which may be used is partially vaporised by the heat liberated on polymerisation. When the catalyst is solid, the heat of reaction can be removed by circulating the reaction mixture in a reactor loop through an external exchanger.

The reaction section is followed by a section in which the catalyst is separated from the effluent, for example by washing with sodium hydroxide followed by washing with water, then by a separation section (for example distillation) where the polymer leaving via line 8 is separated.

When all the effluent leaving step 1 has been treated in step 2, distillation separates a distillate comprising the residual $C_4$ cut which leaves via line 13 (FIG. 1).

When fractionation has been carried out before polymerisation, an effluent comprising the residual $C_4$ cut passes into line 13 (FIG. 2).

The residual $C_4$ cut obtained mainly contains butanes and 2-butene. In the final step 3 of the process (zone 3), the 2-butene is reacted with ethylene (supplied via line 7) to produce propylene (leaving via line 10) by metathesis. Line 9 evacuates the separated by-products.

The metathesis reaction of ethylene with 2-butene can be catalysed by various metal oxides deposited on supports. Preferably, a catalyst is used which comprises at least one rhenium oxide deposited on a support composed of a refractory oxide containing at least alumina, which has an acidic character, such as alumina itself, silica-aluminas or zeolites.

Preferred examples are catalysts comprising rhenium heptoxide deposited on a gamma alumina analogous to that used in reforming catalysts, as described in U.S. Pat. No. 4,795,734. The rhenium content (expressed as rhenium metal) can be in the range 0.01% to 20%, preferably in the range 1% to 15% by weight. The catalysts are, for example, subjected to final thermal activation at a temperature in the range 400° C. to 1000° C. for a period of 10 minutes to 5 hours in a non-reducing atmosphere.

Catalysts comprising rhenium heptoxide deposited on an alumina can also be modified by addition of an oxide of another metal. These modified catalysts contain, for example, rhenium as an oxide, 0.01% to 20% by weight expressed as rhenium metal, deposited on a support containing at least 75% by weight of alumina and 0.01% to 30% by weight of at least one oxide of a metal selected from the group formed by niobium and tantalum, as described in French patent FR-A-2 709 125.

The metathesis reaction is preferably carried out in the liquid phase, in the absence of oxygen, oxygen-containing compounds and moisture, and at a temperature in the range 0° C. to 200° C., preferably in the range 20° C. to 150° C., at a pressure at least equal to that of the vapour tension of the reaction mixture at the reaction temperature.

The catalyst can be used in a fixed bed. However, since it must be regenerated frequently, it would then be necessary to use at least two reactors in parallel, one in operational mode while the other is in regenerational mode. Preferably, a catalytic mobile bed system as described in French patent FR-A-2 608 595 is used.

The catalyst is extracted at regular intervals from the bottom of the reactor and transferred continuously to a regeneration system, from which it is sent to the top of the reactor.

Because of thermodynamic limitations, unconverted ethylene is fractionated in a first distillation column and recycled to the metathesis reactor. A second distillation column separates the propylene and a third column separates the unconverted $C_4$ hydrocarbons which can be recycled to the metathesis reactor, also a small quantity of a heavier fraction.

Figure 3:
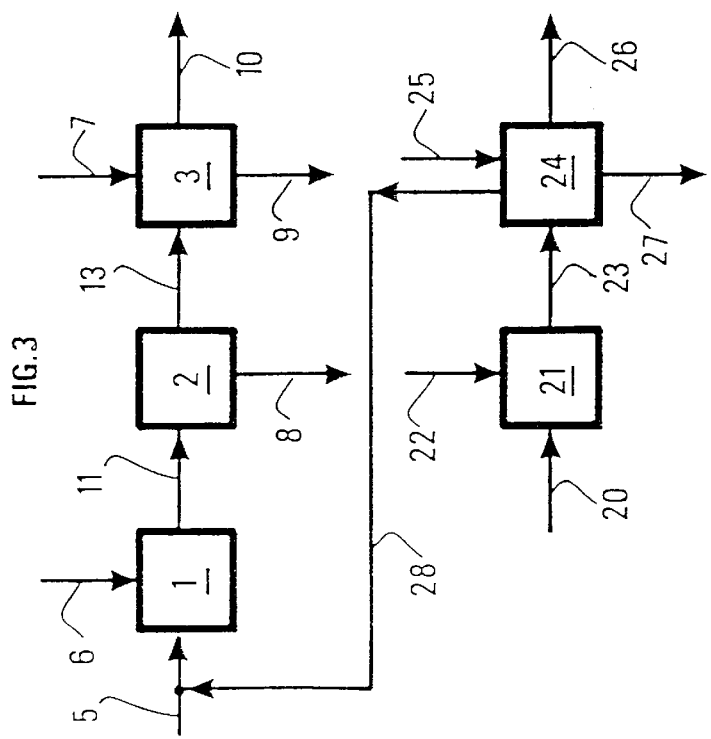

It is highly advantageous to add to the $C_4$ cut treated by the process of the invention, a $C_4$ hydrocarbon effluent, mainly 1-butene and isobutene, from the treatment of a $C_5$ cut by hydroisomerisation then metathesis with ethylene, in accordance with the diagram shown in FIG. 3.

FIG. 3 illustrates this embodiment in which the $C_4$ and $C_5$ cuts are treated simultaneously and separately.

The $C_5$ cut contains mainly pentanes, methylbutenes, pentenes and diolefins containing 5 carbon atoms, accompanied by small quantities of acetylenic hydrocarbons.

The $C_5$ cut entering via line 20 undergoes hydroisomerisation (under the conditions described above for the $C_4$ cut) in a zone 21, hydrogen being introduced via line 22. The effluent leaving via line 23 is at least partially subjected to metathesis in a zone 24 with ethylene supplied via line 25. It is separated: propylene leaves via line 26, by-products leave via line 27, and a mixture of 1-butene and isobutene leaves via line 28.

The mixture of 1-butene and isobutene is carried via line 28 to hydroisomerisaiton zone 1 for the $C_4$ cut. The $C_4$ cut and the mixture are then treated using the process described above.

Figure 4:
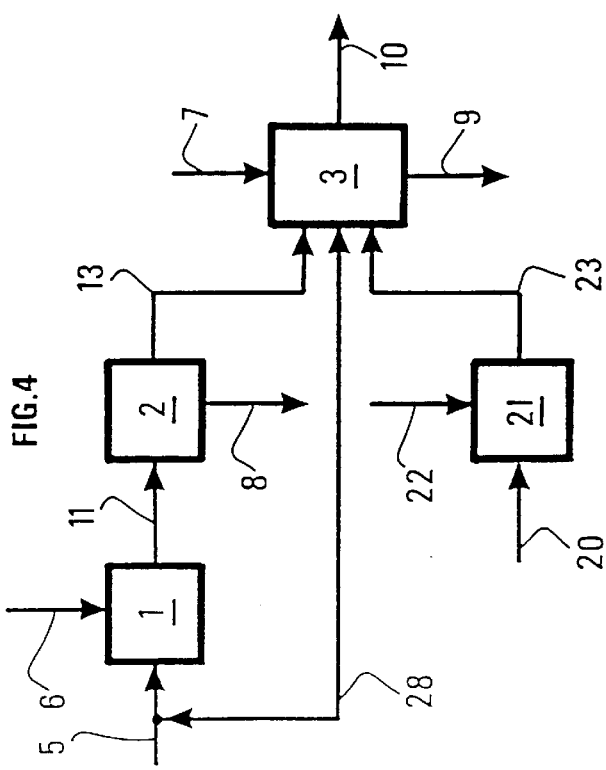

In still more simplified fashion, it may be of advantage to mix the effluent from isobutene polymerisation step 2 (zone 2) in the $C_4$ line, which leaves via line 13, with the effluent from hydroisomerisaiton step 1 (zone 21) for the $C_5$ cut (supplied via line 20) which leaves via line 23, so that only one metathesis operation is required (zone 3), as shown in FIG. 4.

When the process is applied to a steam cracked $C_4$ cut, it may be of advantage to integrate the metathesis unit with the cracker to improve the fractionation string of the latter.

The invention also concerns a plant for carrying out the process described above and which comprises successively:

1) a selective hydrogenation zone 1 with simultaneous isomerisation of 1-butene to 2-butenes, said zone comprising at least one means 5 for introducing a cut to be converted, at least one means 11 for discharging an effluent, and at least one means 6 for introducing hydrogen, said zone also comprising at least one catalyst bed, preferably comprising at least one metal selected from the group formed by nickel, palladium and platinum, and deposited on a support;

2) a polymerisation and separation zone 2 comprising at least one means 11, 12 for introducing isobutene from the effluent from zone 1, at least one means 8 for discharging polymer, and at least one means 13 for discharging a residual $C_4$ cut without polymer, the polymerisation zone containing at least one acid catalyst;

3) a metathesis zone 3 containing at least one catalyst, preferably based on rhenium oxide, and deposited on a support, followed by a separation zone, and comprising at least one means 13 for introducing a residual $C_4$ cut, at least one means 7 for introducing ethylene, at least one means 10 for discharging propylene and at least one means 9 for discharging by-products.

In a first embodiment, zone 2 of step 2 comprises a polymerisation zone followed by at least one separation zone. Advantageously, the polymerisation zone contains an acid catalyst in suspension.

In a preferred embodiment, zone 2 of step 2 is preceded by an isobutene extraction zone 4 and comprises a polymerisation zone followed by at least one separation zone.

Preferably, a mobile catalyst bed is used in zone 3 of step 3.

The plant for carrying out the process can also comprise a section for treating an olefinic $C_5$ cut to produce at least a portion of the $C_4$ cut to be converted, said $C_5$ cut containing diolefins, n-pentenes, methylbutenes and acetylenic impurities in particular, the process comprising successively at least:

1) a selective hydrogenation zone 21 with simultaneous isomerisation of alpha olefins containing 5 carbon atoms to 2-pentenes and 2-methyl-2-butene, said zone comprising at least one means 20 for introducing $C_5$ cut, at least one means 23 for disharging effluent, and at least one means 22 for introducing hydrogen, said zone also comprising at least one bed of a catalyst which preferably comprises at least one metal selected from the group formed by nickel, palladium and platinum, and deposited on a support;

2) a metathesis zone 24 containing at least one catalyst, preferably based on rhenium oxide, deposited on a support, and comprising at least one means 23 for introducing effluent from zone 21, at least one means 25 for introducing ethylene, at least one means 26 for discharging propylene, at least one means 27 for discharging by-products and at least one means 28 for discharging a mixture of 1-butene and isobutene, which is sent to zone 1.

In a particularly interesting embodiment, the $C_4$ and/or $C_5$ cuts originate from an upstream steam cracking zone, the introduction means for the cuts being connected to said steam cracking zone, and the means for introducing ethylene into the metathesis step is connected to said steam cracking zone.

The following examples illustrate the invention without limiting its scope.

EXAMPLE 1

A $C_4$ cut leaving a steam cracker had the composition shown in Table 1 (stream 1). The following abbreviations were used in the Table: MAPD=methylacetylene+propadiene; BBV=1,2-butadiene+1-butyne+vinylacetylene.

Firstly, the $C_4$ cut was hydroisomerised. It was continuously introduced at the mass flow rate shown in Table 1 and at a pressure of 2 MPa into a first reactor comprising a fixed bed of 2.6 T of a catalyst constituted by palladium on alumina which had been sulphurized. Hydrogen (mixed with methane) was also injected into the reactor as shown in Table 1 (stream 2). The temperature, which was 50° C. at the inlet, had risen to 95° C. at the outlet. The effluent was then treated in a finishing reactor charged with 2.5 T of the same catalyst and operating practically isothermally at 70° C. At the outlet (Table 1, stream 3), the cut was free of acetylenic compounds and the 1,3-butadiene had been transformed into mainly butenes, the majority of which were 2-butenes, since the 1-butene had been isomerised. The cut was then treated in a stabilizing column where the residual hydrogen and methane were separated. After this treatment, the cut had the composition of stream 4 (Table 1).

In the second step, the isobutene contained in the hydrotreated cut was polymerised to produce a polymer constituted mainly of isobutene units but also containing small quantities of 1-butene units (polybutene). Stream 4 (Table 1) was introduced into a stirred reactor at the same time as the catalyst constituted by powdered alumninium chloride in an amount of 6 kg/h of $AlCl_3$. The heat of polymerisation was eliminated by circulating the liquid phase in a loop from the reactor through a cooled external exchanger to maintain the temperature of the reaction at −5° C. At the reactor exit, the catalyst was destroyed and separated from the crude effluent by washing with sodium hydroxide followed by washing with water. The catalyst-free crude effluent had the composition given in Table 1 (stream 5). The residual $C_4$ cut and the polybutene were separated by distillation.

In the final step, the residual cut, which contained mainly 2-butenes, was reacted with ethylene (overall composition: stream 6 in Table 1) on a metathesis catalyst constituted by rhenium oxide on gamma alumina (8% by weight of rhenium metal), prepared as described in U.S. Pat. No. 4,795,734. The $C_4$ cut was mixed at the inlet to the metathesis reactor with additional ethylene and with the ethylene and butene recycling streams. This reactor operated as a mobile bed as described in French patent FR-A-2 608 595, at a temperature of 35° C. and at a pressure of 3.5 MPa, and was coupled with a regenerator operating at 550° C. at atmospheric pressure. The catalyst was extracted at regular intervals from the bottom of the reactor and transferred to the regenerator from which it was returned to the top of the reactor, the transfers taking place via buffering traps. At the reactor outlet, unconverted ethylene was fractionated in a first distillation column and recycled. A second distillation column separated the propylene and a third column separated the unconverted $C_4$ hydrocarbons which were also recycled, and small quantities of pentenes. The composition of the metathesis effluent is shown in Table 1, stream 7.

The overall balance of the transformation was determined as follows. For 100 parts by weight (pw) of $C_4$ cut leaving the steam cracker, 1.6 pw of hydrogen and 26.7 pw of ethylene were consumed, and 29.7 pw of polybutene and 79.6 pw of propylene were produced. For the steam cracker from which the treated $C_4$ cut originates, this balance thus represents a small consumption of ethylene, and a large additional production of propylene, without having to modify the operating conditions of the cracker.

EXAMPLE 2

This example describes the use of both a $C_4$ and a $C_5$ steam cracking cut to produce polybutene and propylene.

A $C_5$ cut leaving a steam cracker had the composition shown in Table 2 (stream 1). Firstly, the $C_5$ cut was hydroisomerised and then underwent metathesis in the presence of ethylene to produce propylene and a $C_4$ fraction constituted mainly by isobutene and 1-butene which was mixed with the $C_4$ cut from the cracker.

In the first hydroisomerisation step, the $C_5$ cut was continuously introduced at the mass flow rate shown in Table 2 and at a pressure of 2 MPa into a first reactor comprising a fixed bed of 1.2 T of a catalyst constituted by palladium on alumina which had been sulphurized. Hydrogen (mixed with methane) was also injected into the reactor, as shown in Table 2 (stream 2). The temperature, which was 50° C. at the inlet, had risen to 85° C. at the outlet. The effluent was then treated in a finishing reactor charged with 1.1 T of the same catalyst and operating practically isothermally at 80° C. At the outlet (Table 2, stream 3), the cut was free of traces of acetylenic compounds and the $C_5$ diolefins had been hydrogenated to methylbutenes and pentenes, the majority of which were 2-methyl-2-butene and 2-pentene due to the isomerisation which had occurred at the same time. The cut was then treated in a stabilizing column where the residual hydrogen and methane were separated. After this treatment, the cut had the composition of stream 4 (Table 2).

In the second step, the $C_5$ cut was reacted with ethylene (overall composition: stream 5 in Table 2) over a metathesis catalyst constituted by rhenium oxide on gamma alumina (8% by weight of rhenium metal), prepared as described in U.S. Pat. No. 4,795,734. The metathesis reactor operated as a mobile bed as described in French patent FR-A-2 608 595, at a temperature of 35° C. and at a pressure of 3.5 MPa, and was coupled with a regenerator operating at 550° C. at atmospheric pressure. The catalyst was extracted at regular intervals from the bottom of the reactor and transferred to the regenerator from which it was returned to the top of the reactor, the transfers taking place via buffering traps. At the reactor outlet, unconverted ethylene was fractionated in a first distillation column and recycled. A second distillation column separated the propylene and a third column separated isobutene and 1-butene overhead and heavier olefins from the bottom. The composition of the metathesis effluent is shown in Table 2, stream 6.

The isobutene and 1-butene stream obtained after fractionation of the crude metathesis effluent (Table 3, stream 2) was then mixed with the $C_4$ cut used in Example 1 (Table 3, stream 1). The mixture was subjected to the same succession of steps under the same conditions as described in Example 1. The operational balance is given in Table 3.

The overall balance of the transformation was determined as follows. For 69 parts by weight (pw) of $C_4$ cut and 31 parts by weight (pw) of $C_5$ cut leaving the reactor, 1.5 pw of hydrogen and 23.4 pw of ethylene were consumed, and 24.6 pw of polybutene and 62.7 pw of propylene were produced.

TABLE 1

| (kg/h) | 1 Feed $C_4$ | 2 Feed hydro-isomerisation | 3 Outlet hydro-isomerisation | 4 $C_4$ outlet stabilisation-inlet polybutene | 5 Outlet polybutene | 6 Inlet metathesis | 7 Outlet metathesis |
|---|---|---|---|---|---|---|---|
| (C3 + C3=) | 10 | 10 | 45 | 28 | 28 | | |
| MAPD | 31 | 31 | | | | | |
| Iso + n-butane | 991 | 991 | 1434 | 1404 | 1404 | 1404 | 1404 |
| Isobutene | 5741 | 5741 | 5741 | 5533 | 55 | 55 | 55 |
| 1-butene | 3407 | 3407 | 1003 | 729 | 70 | 70 | 0 |
| 2-butenes | 2250 | 2250 | 12733 | 12630 | 12630 | 12630 | 1642 |
| 1,3-butadiene | 8095 | 8095 | | | | | |
| BBV | 104 | 104 | | | | | |
| Hydrogen | | 343 | 16 | | | | |
| Methane | | 909 | 909 | | | | |
| Polybutene | | | | | 6137 | | |
| Ethylene | | | | | | 5513 | 54 |
| Propylene | | | | | | | 16429 |
| Pentenes | | | | | | | 88 |
| Total | 20629 | 21881 | 21881 | 20324 | 20324 | 19672 | 19672 |

TABLE 2

| (kg/h) | 1 Feed $C_5$ | 2 Feed hydro-isomerisation | 3 Outlet hydro-isomerisation | 4 $C_5$ outlet stabilisation | 5 Inlet metathesis | 6 Outlet metathesis |
|---|---|---|---|---|---|---|
| C4 | 91 | 91 | 91 | 91 | | |
| C5 dienes | 2723 | 2723 | | | | |
| Iso + n-pentane | 4538 | 4538 | 4729 | 4729 | 4729 | 4729 |
| 3-methyl-1-butene | 61 | 61 | 34 | 34 | 34 | 34 |
| 2-methyl-1- | 294 | 294 | 156 | 156 | 156 | 156 |

TABLE 2-continued

| (kg/h) | 1 Feed C$_5$ | 2 Feed hydro-isomerisation | 3 Outlet hydro-isomerisation | 4 C$_5$ outlet stabilisation | 5 Inlet metathesis | 6 Outlet metathesis |
|---|---|---|---|---|---|---|
| butene |  |  |  |  |  |  |
| 2-methyl-2-butene | 734 | 734 | 2070 | 2070 | 2070 | 414 |
| 1-pentene | 248 | 248 | 119 | 119 | 119 | 119 |
| 2-pentene | 252 | 252 | 1174 | 1174 | 1174 | 411 |
| Other C5 | 136 | 136 | 788 | 788 | 788 | 158 |
| olefins |  |  |  |  |  |  |
| Hydrogen |  | 88 | 4 |  |  |  |
| Methane |  | 177 | 177 |  |  |  |
| Ethylene |  |  |  |  | 1238 | 12 |
| Propylene |  |  |  |  |  | 1451 |
| Isobutene |  |  |  |  |  | 1193 |
| 1-butene |  |  |  |  |  | 610 |
| Heavy > C$_5$ |  |  |  |  |  | 1021 |
| Total | 9077 | 9342 | 9342 | 9161 | 10308 | 10308 |

TABLE 3

| (kg/h) | 1 C$_4$ cut | 2 C4 from metathesis of C$_5$ | 3 Feed hydro-isomerisation | 4 Outlet hydro-isomerisation | 5 C$_4$ outlet stabilisation-inlet polybutene | 6 Outlet polybutene | 7 Inlet metathesis | 8 Outlet metathesis |
|---|---|---|---|---|---|---|---|---|
| (C3 + C3=) | 10 |  | 10 | 45 | 28 | 28 |  |  |
| MAPD | 31 |  | 31 |  |  |  |  |  |
| Iso + n-butane | 991 |  | 991 | 1434 | 1404 | 1404 | 1404 | 1404 |
| Isobutene | 5741 | 1193 | 6934 | 6934 | 6683 | 66 | 64 | 64 |
| 1-butene | 3407 | 610 | 4017 | 1047 | 761 | 74 | 74 | 2 |
| 2-butenes | 2250 |  | 2250 | 13310 | 13202 | 13202 | 13202 | 1716 |
| 1,3-butadiene | 8095 |  | 8095 |  |  |  |  |  |
| BBV | 104 |  | 104 |  |  |  |  |  |
| Hydrogen |  |  | 350 | 12 |  |  |  |  |
| Methane |  |  | 909 | 909 |  |  |  |  |
| Polybutene |  |  |  |  |  | 7304 |  |  |
| Ethylene |  |  |  |  |  |  | 5707 |  |
| Propylene |  |  |  |  |  |  |  | 17175 |
| Pentenes |  |  |  |  |  |  |  | 90 |
| Total | 20629 | 1803 | 23691 | 23691 | 22078 | 22078 | 20451 | 20451 |

We claim:

1. A process for the conversion of an olefinic C$_4$ cut to polyisobutene and to propylene, said cut containing mainly diolefins, 1-butene, isobutene and acetylenic impurities, wherein the C4 cut, the isobutene and 1-butene originate at least in part from an olefinic C$_5$ cut, said process comprising the following steps:
   1) selective hydrogenation of the diolefins and acetylenic impurities with simultaneous isomerisation of the C$_5$ alpha olefins to 2-pentenes and 2-methyl-2-butene, by passing said C$_5$ cut in a liquid phase over a catalyst comprising at least one metal selected from the group consisting of nickel, palladium and platinum, deposited on a support, at a temperature of 20°–200° C., a pressure of 1–5 mPa, and a space velocity of 0.5–10 h$^{-1}$, with a H$_2$/diolefin (molar) ratio of 0.5 to 5, to obtain a hydroisomerization effluent containing mainly 2-pentene and 2-methyl-2-butene, and containing a reduced amount of diolefins and acetylenic compounds;
   2) metathesis of at least a portion of the effluent from the preceding step with ethylene, in the presence of a catalyst comprising at least one rhenium oxide deposited on a support, at a temperature in the range 0° C. to 100° C., and at a pressure which is at least equal to the vapor pressure of the reaction mixture at the reaction temperature, to obtain an effluent containing mainly propylene, 1-butene and isobutene, metathesis being followed by separation of the metathesis effluent into the $C_4$ cut containing isobutene and 1-butene and a stream of propylene;

3) subjecting said $C_4$ cut in a second hydroisomerization reactor in a liquid phase by contacting the $C_4$ cut with a catalyst comprising at least one metal selected from the group consisting of nickel, palladium and platinum, deposited on a support, at a temperature of 20°–200° C. a pressure of 105 mPa, and a space velocity of 0.5–10 $h^{-1}$, with a $H_2$/diolefin (molar) ratio of 0.5 to 5, to obtain an effluent pertaining mainly 2-butene and isobutene, and a reduced quantity of diolefins and acetylenic compounds;

4) polymerizing the isobutene contained in the effluent from step (3) to polyisobutene, in the presence of an acid catalyst, at a temperature of −100° C. to +100° C., and at a pressure such that the reaction is carried out in the liquid phase, wherein the isobutene is optionally separated from the other constituents of the effluent from step (3) before polymerization, to obtain (a) polyisobutene and (b) a residual $C_4$ cut without a polymer, 5) subjecting the residual $C_4$ cut to metathesis with ethylene, in the presence of a catalyst comprising at least one rhenium oxide deposited on a support, at a temperature in the range 0° C. to 100° C., and at a pressure which is at least one rhenium oxide deposited on a support, at a temperature in the range 0° C. to 100° C., and at a pressure which is at least equal to the vapor pressure of the reaction mixture at the reaction temperature, to obtain an effluent containing propylene, metathesis being followed by separation of the propylene.

2. A process according to claim 1, wherein step 3) is carried out in the presence of a catalyst containing 0.05% to 10% by weight of sulphur.

3. A process according to claim 1 wherein the catalyst has been treated, before charging it into the second hydroisomerization reactor, with at least one sulphur-containing compound diluted in a solvent, and that the catalyst obtained containing 0.05% to 10% (by weight) of sulphur is charged into the reactor and activated in a neutral or reducing atmosphere at a temperature in the range 20° C. to 300° C., a pressure in the range 0.1 to 5 MPa and a GHSV in the range 50 to 600 $h^{-1}$, and in that the feed is brought into contact with said activated catalyst.

4. A process according to claim 1, wherein the catalyst in step 3 is constituted by palladium deposited on alumina and containing sulphur.

5. A process according to claim 1, wherein the isobutene is polymerised in the presence of a Lewis acid catalyst selected from the group consisting of aluminium chloride, boron trifluoride, chloroalkylaluminium compounds and tin tetrachloride.

6. A process according to claim 5, wherein the isobutene is polymerised in the presence of said Lewis acid catalyst associated with traces of a Bronsted acid.

7. A process according claim 1, wherein metathesis in step 5 takes place in the presence of a catalyst containing a rhenium oxide in a proportion of 0.01% to 20% by weight, expressed as rhenium metal, deposited on a support containing at least 75% by weight of alumina and 0.01% to 30% by weight of at least one oxide of a metal selected from the group consisting of by niobium and tantalum.

8. A process according to claim 1, wherein metathesis in step 5 is carried out with a catalyst in a mobile bed.

9. A process according to claim 1, characterized in that the $C_4$ and $C_5$ cuts originate from a steam cracking unit.

10. A process according to claim 9, characterized in that single metathesis step simultaneously treats the effluent from the $C_5$ cut and the $C_4$ cut.

* * * * *